US007537737B2

(12) United States Patent
Abe et al.

(10) Patent No.: US 7,537,737 B2
(45) Date of Patent: May 26, 2009

(54) INSTALLATION STRUCTURE FOR GAS SENSOR

(75) Inventors: Hiroyuki Abe, Utsunomiya (JP); Akihiro Suzuki, Utsunomiya (JP); Takashi Sasaki, Shioya-gun (JP)

(73) Assignee: Honda Motor Co., Ltd. (JP)

( * ) Notice: Subject to any disclaimer, the term of this patent is extended or adjusted under 35 U.S.C. 154(b) by 396 days.

(21) Appl. No.: 10/401,374

(22) Filed: Mar. 28, 2003

(65) Prior Publication Data
US 2003/0190261 A1    Oct. 9, 2003

(30) Foreign Application Priority Data
Apr. 4, 2002   (JP) .............................. 2002-102877

(51) Int. Cl.
| B01L 9/00 | (2006.01) |
| G01N 21/00 | (2006.01) |
| G01N 27/00 | (2006.01) |
| G01N 31/00 | (2006.01) |
| G01N 33/00 | (2006.01) |

(52) U.S. Cl. .......................... 422/104; 422/83; 422/94; 422/95; 422/97; 422/98; 422/100; 422/103; 436/139; 436/143; 436/144; 436/149; 436/155; 436/159; 73/1.01; 73/1.02; 73/23.2; 73/23.31; 73/23.32

(58) Field of Classification Search ................ 73/1.01, 73/1.02, 23.2, 23.31, 23.32; 422/83, 94, 422/95, 97, 98, 100, 103, 104; 436/139, 436/143, 144, 149, 155, 159; 29/592, 592.1
See application file for complete search history.

(56) References Cited

U.S. PATENT DOCUMENTS

| 4,208,266 A | * | 6/1980 | Auman et al. ............... 204/410 |
| 4,617,795 A | | 10/1986 | Abthoff et al. |
| 4,903,648 A | * | 2/1990 | Lassankse ................. 123/65 R |
| 5,236,330 A | * | 8/1993 | Buchheister et al. .......... 60/276 |
| 5,389,223 A | * | 2/1995 | Hoetzel ...................... 204/425 |
| 5,614,658 A | * | 3/1997 | Moss ........................ 73/23.31 |
| 5,682,870 A | * | 11/1997 | Motoyama ................... 123/703 |
| 5,795,545 A | * | 8/1998 | Koripella et al. .............. 422/94 |
| 5,832,723 A | * | 11/1998 | Iwata et al. ................... 60/276 |
| 5,836,155 A | * | 11/1998 | Katoh .......................... 60/276 |
| 6,319,378 B1 | | 11/2001 | Kojima et al. |
| 6,581,180 B1 | * | 6/2003 | Weng ........................ 714/781 |
| 6,770,391 B2 | * | 8/2004 | Nelson et al. ................. 429/22 |
| 6,848,438 B2 | * | 2/2005 | Celerier et al. .............. 123/672 |

FOREIGN PATENT DOCUMENTS

| EP | 1452853 A1 | 5/2003 |
| GB | 2067294 A | * 7/1981 |

(Continued)

*Primary Examiner*—Brian J Sines
(74) *Attorney, Agent, or Firm*—Fish & Richardson P.C.

(57) ABSTRACT

An installation structure for a gas sensor capable of detecting gas concentration in a highly accurate manner is provided. The installation structure for a gas sensor which detects concentration of gas circulating inside an outlet-side piping comprises a through hole 18 in an inner wall of the outlet-side piping and the gas sensor comprises a gas inlet portion with one face open within the outlet-side piping 14, and the gas sensor is installed to the outlet-side piping in a condition where the gas inlet portion does not protrude from the inner wall of outlet-side piping.

3 Claims, 5 Drawing Sheets

FOREIGN PATENT DOCUMENTS

| | | |
|---|---|---|
| JP | 60-210750 | 10/1985 |
| JP | 63-030751 | 2/1988 |
| JP | 06-40853 | 5/1994 |
| JP | 06-223850 | 8/1994 |
| JP | HEI 6-223850 | 8/1994 |
| JP | 07-055740 | 3/1995 |
| JP | 09-005279 | 1/1997 |
| JP | HEI 9-5278 | 1/1997 |
| JP | HEI 9-170994 | 6/1997 |
| JP | 9-243582 | 9/1997 |
| JP | 10-010084 | 1/1998 |
| JP | 11-352086 | 12/1999 |
| JP | 2000-46775 | 2/2000 |
| JP | 2001-137708 | 1/2002 |
| JP | 2002-071615 | 3/2002 |
| JP | 2002-110214 | 4/2002 |
| JP | 2003-294675 | 10/2003 |
| WO | WO 01/04316 A2 | 6/2001 |
| WO | WO 01/43216 A2 | 6/2001 |
| WO | WO 03/096000 A1 | 11/2003 |
| WO | WO 03/096001 A1 | 11/2003 |

\* cited by examiner

INSTALLATION STRUCTURE FOR GAS SENSOR

BACKGROUND OF THE INVENTION

1. Field of the Invention

The present invention relates to an installation structure for a gas sensor, which can perform accurate detection.

2. Description of the Related Art

As an installation structure for a gas sensor, there is for example that shown in Japanese Unexamined Patent Application, First Publication No. Hei 9-5278. Explaining this by means of FIG. 7, reference symbol 41 denotes a sensor base. On the surface side of the sensor base 41 is formed a gas detection mechanism 44 which is provided with a reference element 42 and a detection element 43, and these are covered by a cover 45. The top of the cover 45 is of reduced diameter, with a cylindrical cavity end opening blocked by a flow velocity reducing member 46. An empty space within a reduced diameter cylinder wall 47 is formed as a deceleration inlet 48. Moreover, the base end side within the cover 45 is configured as a diffusion chamber 49.

A gas sensor S constructed in this way is attached along the sensor base 41 to an outer wall of a target detection gas passage 50 so as to protrude inside the passage 50.

Also, for example, an installation structure for a gas sensor shown in Japanese Unexamined Patent Application, First Publication No. Hei 9-170994 is known. As shown in FIG. 8, a sensor installation box 54 is attached in a position corresponding to a gas inlet port 53 in an outer wall 52 of a target detection gas passage 50, and by matching a communicating hole 55 of the sensor installation box 54 with the gas inlet port 53, the sensor installation box 54 is communicated with the interior of the passage 50, and a gas sensor S' is attached to a bottom wall 56 of the sensor installation box 54.

The former installation structure is superior in the point that influence from the flow velocity of the target detection gas is suppressed as much as possible, so that conditions in which there is no flow velocity in the diffusion chamber 49 can be created. However, in relation to the cover 45 protruding into the passage 50, there is a problem in that this causes disturbance of the target detection gas flowing through the passage 50, so that concentration fluctuations arise in the target detection gas taken in to inside the cover 45, before arriving at the diffusion chamber 49, and hence accurate detection is not possible.

On the other hand, the latter installation structure has the advantage of being able to detect with minimal influence from the flow velocity, by retaining the target detection gas inside the sensor installation box 54 under conditions where there is no flow velocity. However, there is the problem in that when stagnation arises inside the sensor installation box 54 due to the target detection gas not being replaced enough inside the comparatively wide sensor installation box 54, is not possible to obtain an accurate gas concentration measure of the target detection gas passing through the passage 50 at that time.

SUMMARY OF THE INVENTION

This invention proposes a gas sensor installation structure which can perform accurate detection.

In order to solve the above problem, the invention according a first aspect is an installation structure for a gas sensor (for example the gas sensor 15 in the embodiment) which detects concentrations of gas circulating inside piping (for example the outlet-side piping 14 in the embodiment), wherein there is provided an opening (for example the through hole 18 in the embodiment) in an inner wall of the piping, and there is provided a gas inlet portion (for example the gas inlet portion 25 in the embodiment) in the gas sensor with one face open within the piping, and the gas sensor is attached to the piping in a condition where the gas inlet portion does not protrude from the inner wall of the piping.

By constructing in this manner, since the gas sensor is attached in a condition where the gas inlet portion does not protrude from the inner wall of the piping, then compared to the case where this protrudes into the passage, there is no disturbance to the flow of gas circulating inside the piping, and uniform accurate gas concentration detection can be performed.

Also, because the gas inlet portion with one face open is provided within the piping, then compared to the case in which the gas inlet portion is provided in multiple sites, pressure loss of gas circulating in the piping is reduced, and as well as contributing to power conservation, gas concentration can be accurately measured in a stable state.

The invention according to a second aspect is characterized in that the opening is a through hole, and the gas sensor is attached to the piping from outside the piping by inserting a protruding gas inlet portion into the through hole, and securing flanges (for example the flanges 20 in the embodiment) of the gas sensor, which are provided extending to the front and rear of the gas inlet portion in the gas flow direction, to the piping by means of fasteners (for example the bolts 21 in the embodiment).

By constructing in this manner, the gas sensor can be easily attached when positioned from the exterior of the piping, and in the condition with the gas inlet portion inserted into the through hole, the flanges of the gas sensor can be well balanced and reliably attached to the piping.

The invention according to a third aspect is characterized in that the gas circulating inside the piping is off-gas from a cathode-side of a solid polymer electrolyte fuel cell (for example the fuel cell 10 in the embodiment) and the gas sensor is attached to the upper side of the piping in a direction of a gravity.

By constructing in this manner, even if moisture contained within the cathode-side off-gas condenses when the off-gas temperature is less than 100° C., the sensor located in the upper side of the piping will not be touched directly by droplets of condensed water, so there is no reduction in detection accuracy.

The invention according to a fourth aspect is characterized in that the gas sensor is a catalytic combustion-type hydrogen gas sensor.

Accordingly, for example, in the case where hydrogen gas permeate penetrates the solid polymer electrolyte membrane from the anode side to the cathode side in the solid polymer electrolyte fuel cell, this can be detected rapidly and with high accuracy.

DETAILED DESCRIPTION OF THE INVENTION

Figure 1:
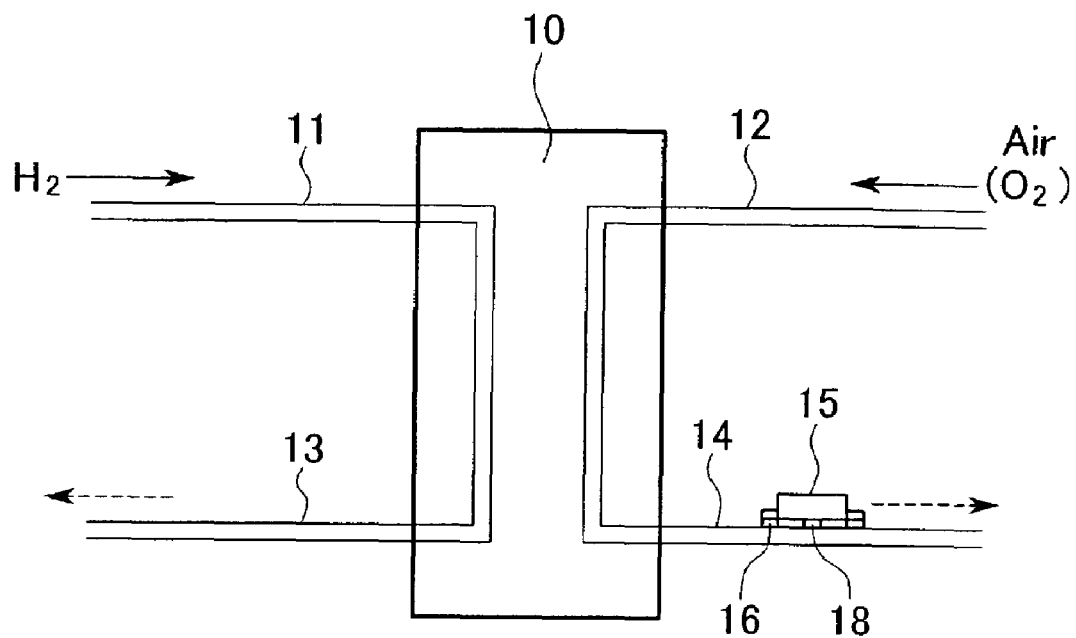
FIG. 1 is a schematic explanatory diagram of a fuel cell system of an embodiment of this invention.

Hereunder is a description of embodiments of the present invention, together with the attached drawings. FIG. 1 is a schematic illustration of a fuel cell system.

A fuel cell 10 for example is a so-called solid polymer electrolyte fuel cell, comprising a plurality of fuel cell units (not shown) each having an electrode assembly composed of an anode-side electrode and a cathode-side electrode, which is further sandwiched between a pair of separators. Hydrogen from a hydrogen-containing fuel gas supplied to the anode-side electrode from inlet-side piping 11 is ionized over a catalytic electrode, and migrates to the cathode-side electrode through a moderately humidified solid polymer electrolyte membrane. Electrons created at this time are sent to an external circuit and used as direct current electrical energy. In the cathode-side electrode, for example, since oxidizing gas containing oxygen, or air is supplied through the inlet-side piping 12, then in this cathode-side electrode, hydrogen ions, electrons and oxygen react and water is generated. Then, from the outlet-side piping 13 and 14 on both the anode-side and the cathode-side, a reacted so-called off-gas is discharged to outside the system. Here, the operating temperature of the solid polymer electrolyte fuel cell 10 is 60° C. to 90° C., and because the cathode-side off-gas temperature is lower than the operating temperature, the reaction generated water contained within can condense.

A catalytic combustion method gas sensor 15 constituting the gist of this invention is attached to a straight section of the outlet-side piping 14 on the cathode side, and occurrences of hydrogen gas being discharged from the outlet-side piping 14 on the cathode side are able to be confirmed by this gas sensor 15.

More specifically, installation seat 16 are provided in an upper side in the gravitational direction of the outlet-side piping 14 on the cathode side, and a through hole (opening) 18, which opens to inside the outlet-side piping 14, is formed in upside of the outlet-side piping 14, and the gas sensor 15 is attached here. Accordingly, the gas sensor 15 becomes attached to the upside of the outlet-side piping 14 in the direction of gravity.

Figure 2:
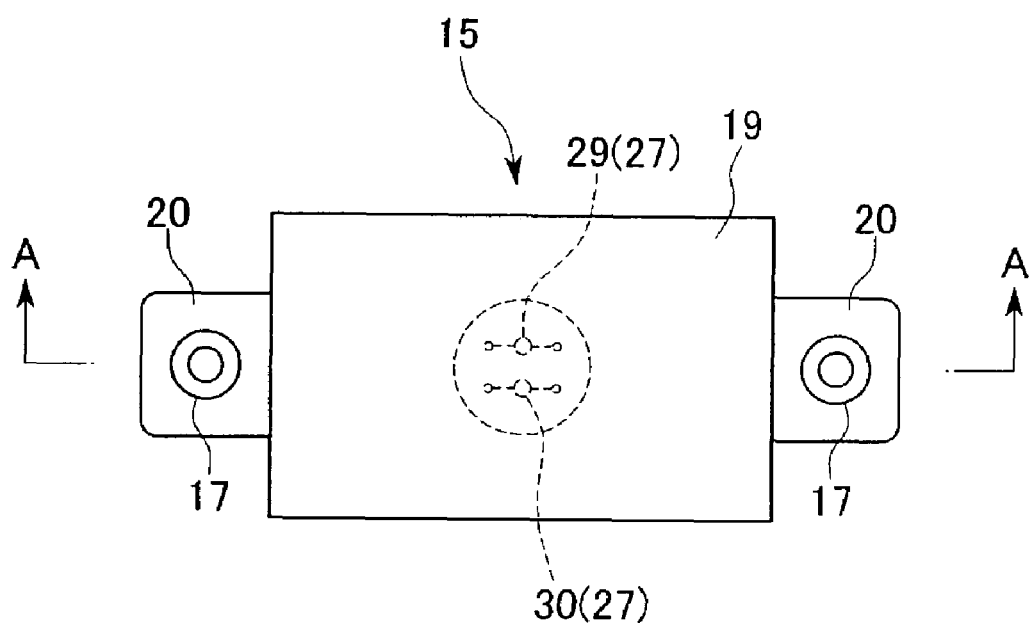
FIG. 2 is a plan view of the gas sensor of the embodiment.
Figure 3:
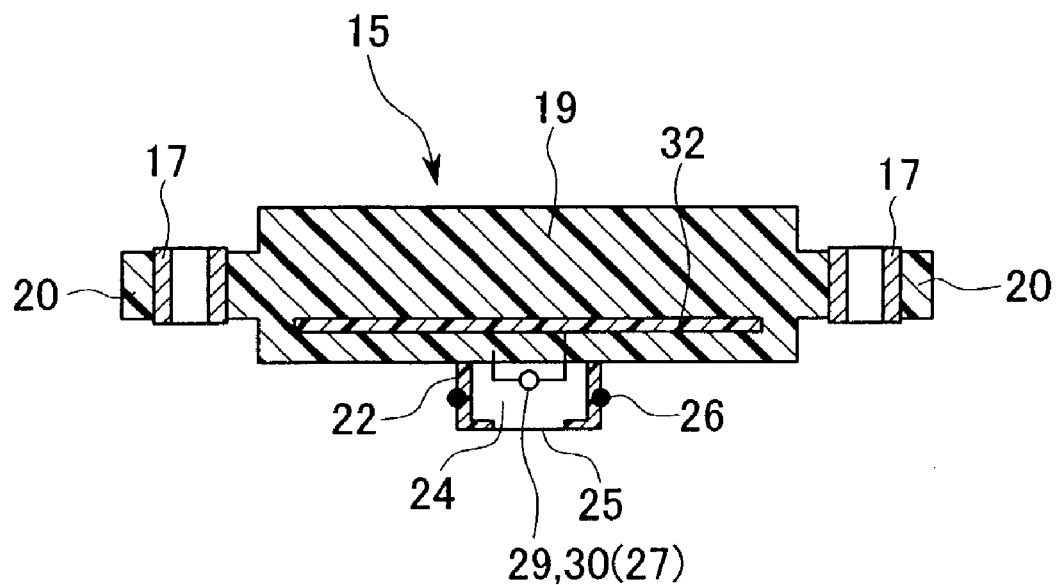
FIG. 3 is a schematic cross-section through the line A-A of FIG. 2.
Figure 4:
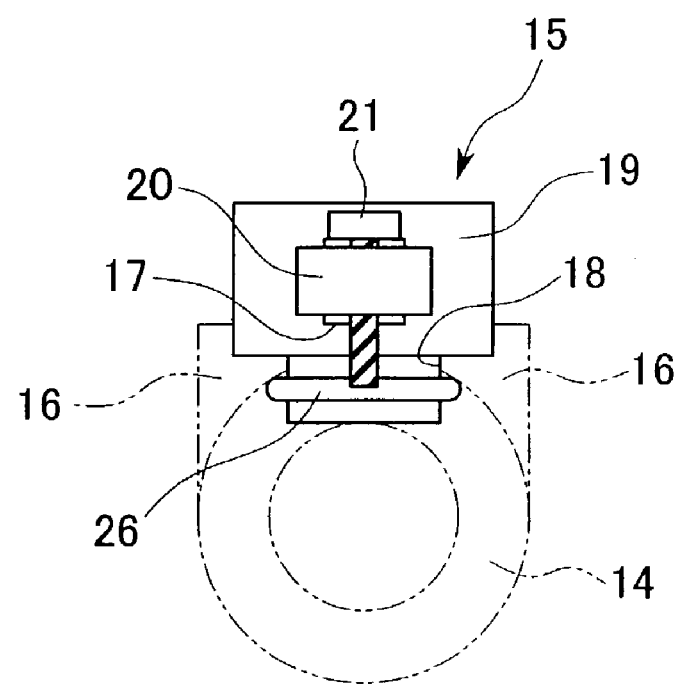
FIG. 4 is a side view of the gas sensor of the embodiment.
Figure 5:
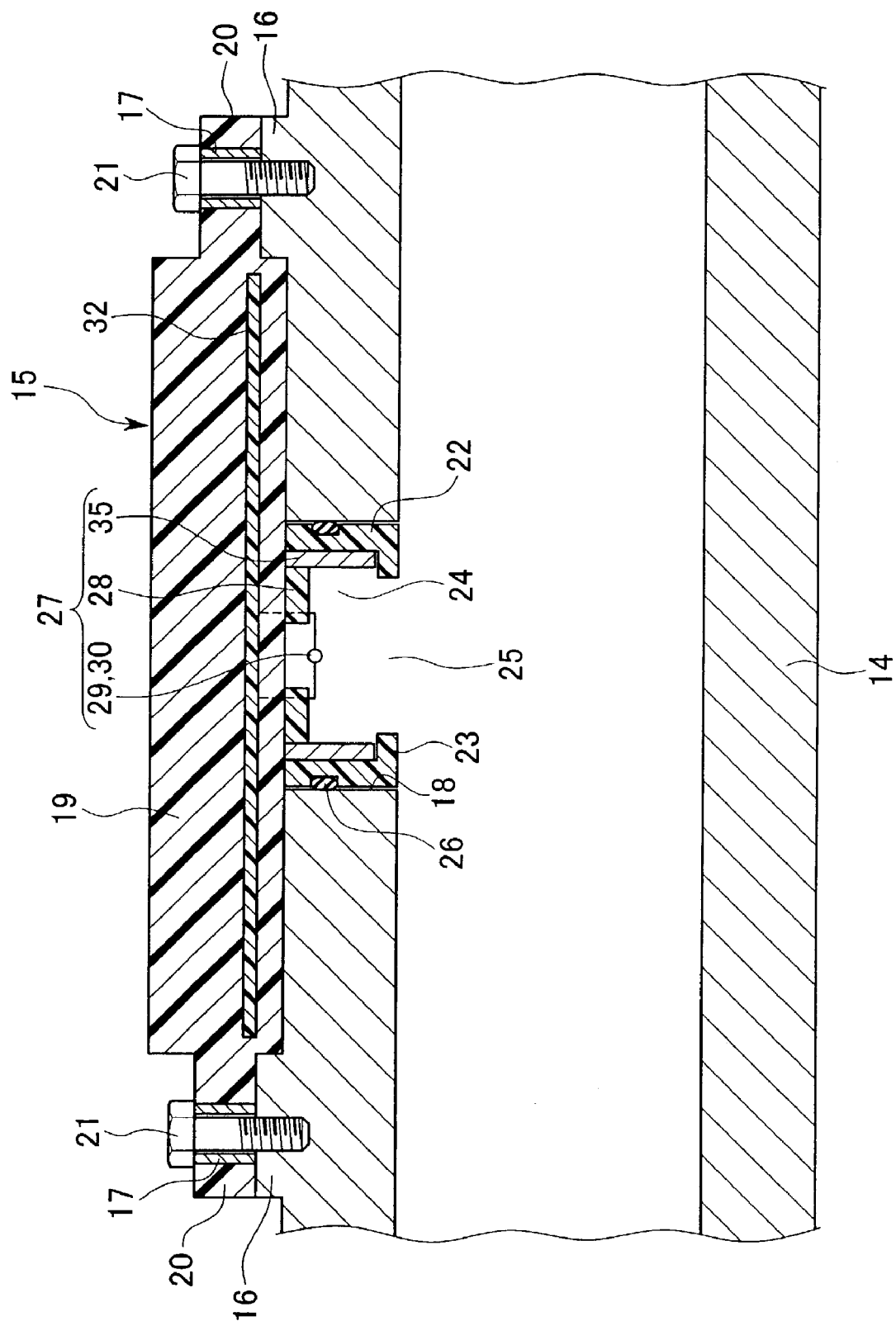
FIG. 5 is a detailed cross-section showing a mounted state of the gas sensor of the embodiment.

FIG. 2 is a plan view of the gas sensor, FIG. 3 is a schematic cross-section view through the line A-A of FIG. 2, FIG. 4 is a side view of FIG. 3, and FIG. 5 is a detailed cross-section view showing the gas sensor attached.

The gas sensor 15 is provided with a long rectangular-shaped casing 19 along the longitudinal direction of the outlet-side piping 14. The casing 19 is made for example from polyphenylene sulfide, and is provided with flanges 20 on both lengthwise ends. The flanges 20 are fitted with collar 17. Bolts (fasteners) 21 are inserted inside the collars 17, so that the gas sensor 15 is fastened and secured to the installation seat 16 of the outlet-side piping 14. That is, the flanges 20 are provided on the casing 19 of the gas sensor 15, so as to extend to the front and rear of the gas inlet portion 25 (mentioned subsequently) in the gas flow direction, and these flanges 20 are secured to the outlet-side piping 14 by the bolts 21.

On the underside of the casing 19, a protruding cylindrical part 22 is formed, passing through the through hole 18 of the outlet-side piping 14 from the outside. Inside the casing 19 as shown in FIG. 3 a circuit board 32 sealed by resin is provided, and a detection element 29 and a temperature compensating element 30 (mentioned subsequently) are connected to this circuit board 32. The interior of the cylindrical part 22 is formed as a gas detecting chamber 24, with an inwards facing flange 23 formed on the face of the gas detecting chamber 24 on the inside of the outlet-side piping 14, and an inner peripheral portion of the flange 23 is formed with an opening serving as a gas inlet portion 25. That is, the gas inlet portion 25 is the part where one face of the gas detecting chamber 24 is open within the outlet-side piping 14.

Moreover, this gas inlet portion 25 is set up so as to be flush with the inner wall of the outlet-side piping 14, or located at a position secluded a little from the external wall. Accordingly, the gas inlet portion 25 is orientated in a perpendicular direction to the off-gas circulating through the outlet-side piping 14. Because of this, the off-gas circulating through the outlet-side piping 14 does not strike the gas inlet portion 25 directly, and so a reduction in detection accuracy can be prevented.

Furthermore, on the outer peripheral surface of the cylindrical part 22, a sealing material 26 for example an O-ring or the like is attached which closely contacts the inner peripheral wall of the through hole 18 to maintain gas tightness. By using the sealing material 26 in this way, the gas sensor 15 can be attached in such a way that the parts of the gas sensor 15 fastened to the outlet-side piping 14 do not directly contact the target detection gas, and hence places where corrosion is generated due to surface treatment of the outlet-side piping 14 peeling off can be eliminated. Moreover, the sensor body 27 is mounted in the interior of the cylindrical part 22.

The sensor body 27 is provided with an annular base 28, made for example from polyphenylene sulfide, in a position blocking the other end of the cylindrical part 22 on the casing 19 side, and is provided on an outer peripheral portion with a peripheral wall 35 of a metal cylinder having a height reaching to the flange 23. The high temperature detection element 29 and the temperature compensating element 30 are provided as a pair passing through the base 28 and separated by a predetermined spacing from the base 28, at the same height.

The detection element 29 is a well known element, being the detection part of a catalytic combustion method gas sensor 15 which uses the heat of combustion when hydrogen, a target detection gas, contacts a catalyst of platinum or the like, and uses a difference in electrical resistance arising between the high temperature detection element 29 and the temperature compensating element 30 in atmospheric temperature, to detect hydrogen gas concentration. This gas sensor 15 can also detect concentrations other than of hydrogen, such as carbon monoxide and methane.

According to the above embodiment, because the gas inlet portion 25 is attached so as to not protrude from the inner wall of the outlet-side piping 14, more specifically, is flush with the inner wall of the outlet-side piping 14, or is located at a position a little secluded from the external wall, then compared to cases where it is protruding from the interior of the outlet-side piping 14, there is no disturbance to the flow of gas circulating within the outlet-side piping 14, and uniform accurate concentration detection can be performed.

Also, because the gas inlet portion 25 opens within the outlet-side piping 14 as one face of the gas detection chamber 24, then compared to the gas inlet portion 25 being provided in multiple sites, pressure loss of the gas circulating in the outlet-side piping 14 can be reduced, and as well as contributing to power conservation, gas concentration can be accurately measured in a stable state.

Because the cylindrical part 22 of the gas sensor 15 is inserted into the through hole 18 from the outside of the outlet-side piping 14, positioning can be easily performed, and the gas sensor 15 can be easily attached from the exterior of the outlet-side piping.

Also, in the condition with the gas inlet portion 25 inserted into the through hole 18, because the gas sensor 15 is attached to the outlet-side piping 14 by securing the flanges 20, which are provided so as to extend to the front and rear in the gas flow direction of the gas inlet portion 25, to the installation seat 16 of the outlet-side piping 14 by the bolts 21, the flanges 20 of the gas sensor 15 can be well balanced and reliably attached to the outlet-side piping 14. Accordingly, attachment failure and the like does not arise.

Moreover, the gas circulating inside the outlet-side piping 14 is cathode-side off-gas of the solid polymer electrolyte fuel cell 10, and because the gas sensor 15 is attached to the gravitational direction upper side of the outlet-side piping 14, then even if moisture contained in the cathode-side off-gas condenses, there is the advantage that the gas sensor 15 which is located on the upper side of the outlet-side piping 14 is not touched by droplets of condensed water.

Also, because the gas sensor 15 is a catalytic combustion method gas sensor, then in the case where hydrogen penetrates the solid polymer electrolyte membrane from the anode side to the cathode side in the solid polymer electrolyte fuel cell 10, this can be detected rapidly and with high accuracy.

Figure 6:
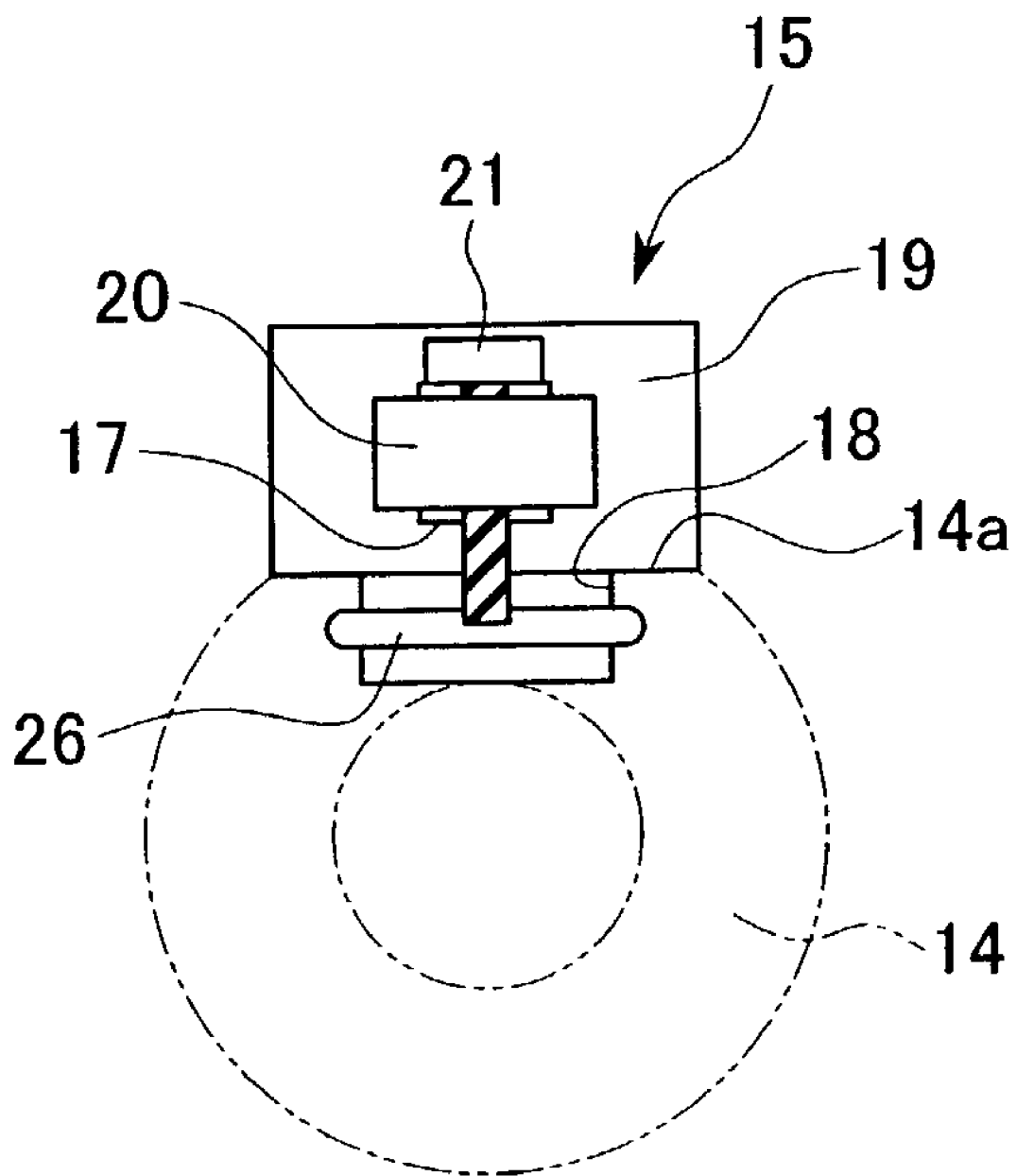
FIG. 6 is a side view corresponding to FIG. 4, of another embodiment of the invention.
Figure 7:
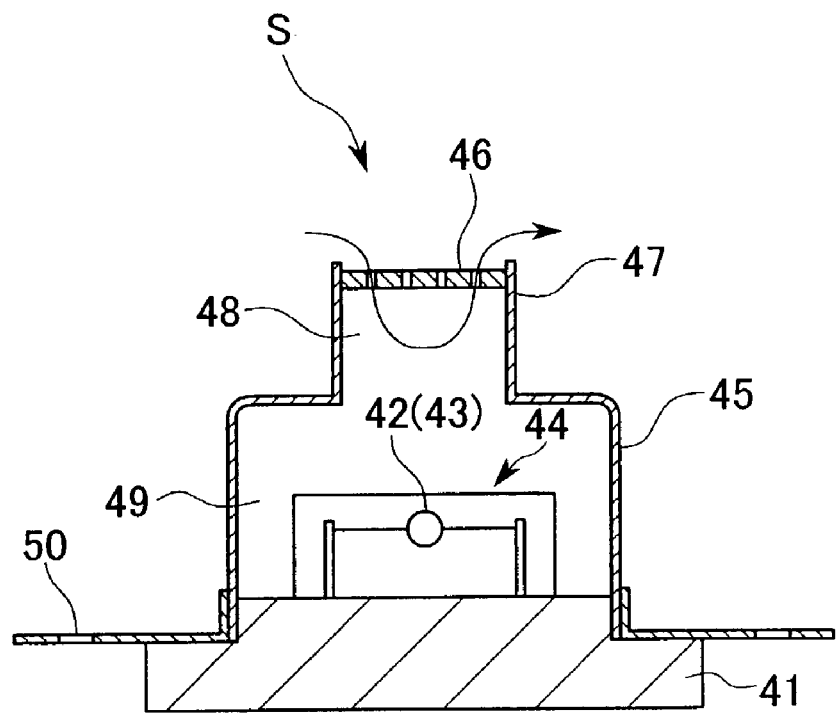
FIG. 7 is a cross-section of conventional technology.
Figure 8:
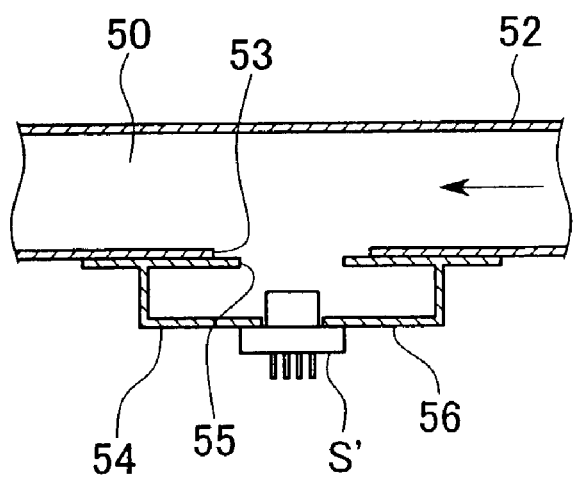
FIG. 8 is a cross-section of another conventional technology.

Furthermore, this invention is not limited to the above embodiment, and it is possible, for example, when attaching the gas sensor 15 to the outlet-side piping 14, as shown in FIG. 6, to remove part of the peripheral wall of the outlet-side piping 14 and here provide a flat surface 14a, and attach the gas sensor 15 to this flat surface 14a. As a result, there is the advantage that there is no need for special piping to form especially the installation seat 16 as in the above embodiment, and a standard thick wall piping material can be used. In FIG. 6, parts the same as in FIG. 4 are denoted by the same reference symbols and description is omitted.

Also, in the inner wall of the outlet-side piping 14, if it is possible to provide a gas inlet portion 25 in the gas sensor 15 with one face opening to within the outlet-side piping 14, and to attach the gas sensor 15 so that the gas inlet portion 25 does not protrude from the inner wall of outlet-side piping 14, it may be possible to attach the gas sensor 15 from the inside of outlet-side piping 14 without the through hole 18.

As described above, according to the first aspect of the invention, the gas sensor is attached so that the gas inlet portion does not protrude from the inner wall of the piping. Therefore, compared to the case in which it protrudes into the flowpath, there is no disturbance to the flow of gas circulating inside the piping, and uniform accurate concentration detection can be performed.

Also, because the gas inlet portion which opens at one face is provided within the piping, then compared to the case in which the gas inlet portion is provided in multiple sites, pressure loss of gas circulating in the piping is reduced, and as well as contributing to power conservation, gas concentration can be accurately measured in a stabilized state.

According to the second aspect of the invention, in addition to the above effects, the gas sensor can be easily attached when positioned from the exterior, and in the condition with the gas inlet portion inserted into the through hole, the flanges of the gas sensor can be well-balanced and reliably attached to the piping.

According to the third aspect of the invention, in addition to the above effects, even if moisture contained within the cathode-side off-gas condenses when the off-gas temperature is less than 100° C., the sensor located in the upper side of the piping will not be touched directly by droplets of condensed water, so there is no reduction in detection accuracy.

According to the fourth aspect of the invention, in addition to the above effects, for example in the case where hydrogen penetrates the solid polymer electrolyte membrane from the anode side to the cathode side in the solid polymer electrolyte fuel cell, this can be detected rapidly and with high accuracy.

What is claimed is:

1. An installation structure of a gas sensor which detects concentrations of gas circulating inside piping, the installation structure comprising:
    a catalytic combustion method hydrogen gas sensor,
    an opening provided in an inner wall of the piping, and the gas sensor comprises a gas inlet opening which opens inside of the gas piping directly,
    wherein said gas sensor is installed to the piping in a condition where said gas inlet portion does not protrude from the inner wall surface of the piping,
    wherein the piping is coupled to a cathode-side of a solid polymer electrolyte fuel cell such that the gas circulating inside the piping is discharged from the cathode-side of the solid polymer electrolyte fuel cell, and
    wherein said gas sensor is installed at an upper portion of the piping relative to the direction of gravity.

2. An installation structure for a gas sensor according to claim 1, wherein said opening is a through hole, and the gas sensor is installed to the piping from outside of the piping by inserting a protruding gas inlet portion into said through hole, and securing flanges of the gas sensor, which are provided extending to the front and rear of the gas inlet portion in the gas flow direction, to the piping by means of fasteners.

3. The installation structure of claim 1 wherein the gas sensor comprises:
    a casing;
    a cylindrical part that protrudes from the casing, wherein the cylindrical part includes an inwardly facing flange that defines the gas inlet opening at a distal end of the cylindrical part; and
    a detection element positioned inside the cylindrical part,
    wherein the cylindrical part is adapted to mate with the opening so that the inwardly facing flange is substantially flush with the inner wall of the piping.

* * * * *